United States Patent [19]
Gilbert et al.

[11] Patent Number: 5,507,814
[45] Date of Patent: Apr. 16, 1996

[54] ORTHOPEDIC IMPLANT WITH SELF-REINFORCED MANTLE

[75] Inventors: Jeremy L. Gilbert, Downers Grove; Eugene P. Lautenschlager, Skokie; Richard L. Wixson, Evanston, all of Ill.

[73] Assignee: Northwestern University, Evanston, Ill.

[21] Appl. No.: 220,242

[22] Filed: Mar. 30, 1994

[51] Int. Cl.$^6$ .................................................. A61F 2/28
[52] U.S. Cl. .................... 623/16; 623/18; 623/22; 623/23; 606/76
[58] Field of Search .................... 623/16, 18, 22, 623/23; 606/76

[56] References Cited

U.S. PATENT DOCUMENTS

| | | | |
|---|---|---|---|
| 2,609,320 | 9/1952 | Modigliani | 623/1 |
| 3,992,725 | 11/1976 | Homsy | 3/1 |
| 4,089,071 | 5/1978 | Kalnberz et al. | 623/16 |
| 4,280,233 | 7/1981 | Raab | 623/18 |
| 4,491,987 | 1/1985 | Park | 3/1.91 |
| 4,718,910 | 1/1988 | Draenert | 623/16 |
| 4,735,625 | 4/1988 | Davidson | 623/16 |
| 4,743,257 | 5/1988 | Tormala et al. | 623/16 |
| 4,851,004 | 7/1989 | Homsy | 623/16 |
| 4,895,573 | 1/1990 | Koeneman et al. | 623/23 |
| 4,963,151 | 10/1990 | Ducheyne et al. | 623/16 |
| 5,037,442 | 8/1991 | Wintermantel et al. | 623/23 |
| 5,080,680 | 1/1992 | Mikhail et al. | 623/23 |
| 5,171,288 | 12/1992 | Mikhail et al. | 623/23 |
| 5,180,395 | 1/1993 | Klaue | 623/23 |
| 5,197,990 | 3/1993 | Lawes et al. | 623/23 |

OTHER PUBLICATIONS

B. M. Fishbane et al., Stainless Steel Reinforcement of Polymethylmethacrylate, Clin. Orthop. Rel. Res. 128:194 (1977).
M. Pilliar et al., Carbon–Reinforced Bone Cement in Orthopedic Surgery, J. Biomed. Mater. Res., 10:893 (1976).
S. Saha et al., Improved Properties of Aramid Fiber Reinforced Polymethylmethacrylate, Trans., 4:21 (1981).
Buckley et al., Deformation Processing of PMMA into High–Strength Fibers, J. Applied Pol. Sci., 44:1321–1330 (1992).

*Primary Examiner*—Paul Prebilic
*Attorney, Agent, or Firm*—Tilton Fallon Lungmus

[57] ABSTRACT

An orthopedic implant, such as the bone-implantable portion of a joint prosthesis, in which a rigid stem is dimensioned to be received in the intramedullary canal of a bone, and in which the stem has at least a portion of its length encased in a preformed mantle consisting of a self-reinforced poly(methylmethacrylate) fiber composition where the fibers are oriented in predetermined directions with respect to the axis of the stem, are of a diameter within the range of about 5 to 500 microns ($\mu$m), and have aligned molecular chains that provide such fibers with longitudinal heat relaxation ratios of no less than about 6 to 1 is disclosed. Also disclosed are the methods for making such an implant and for securing it in an intramedullary canal.

16 Claims, 2 Drawing Sheets

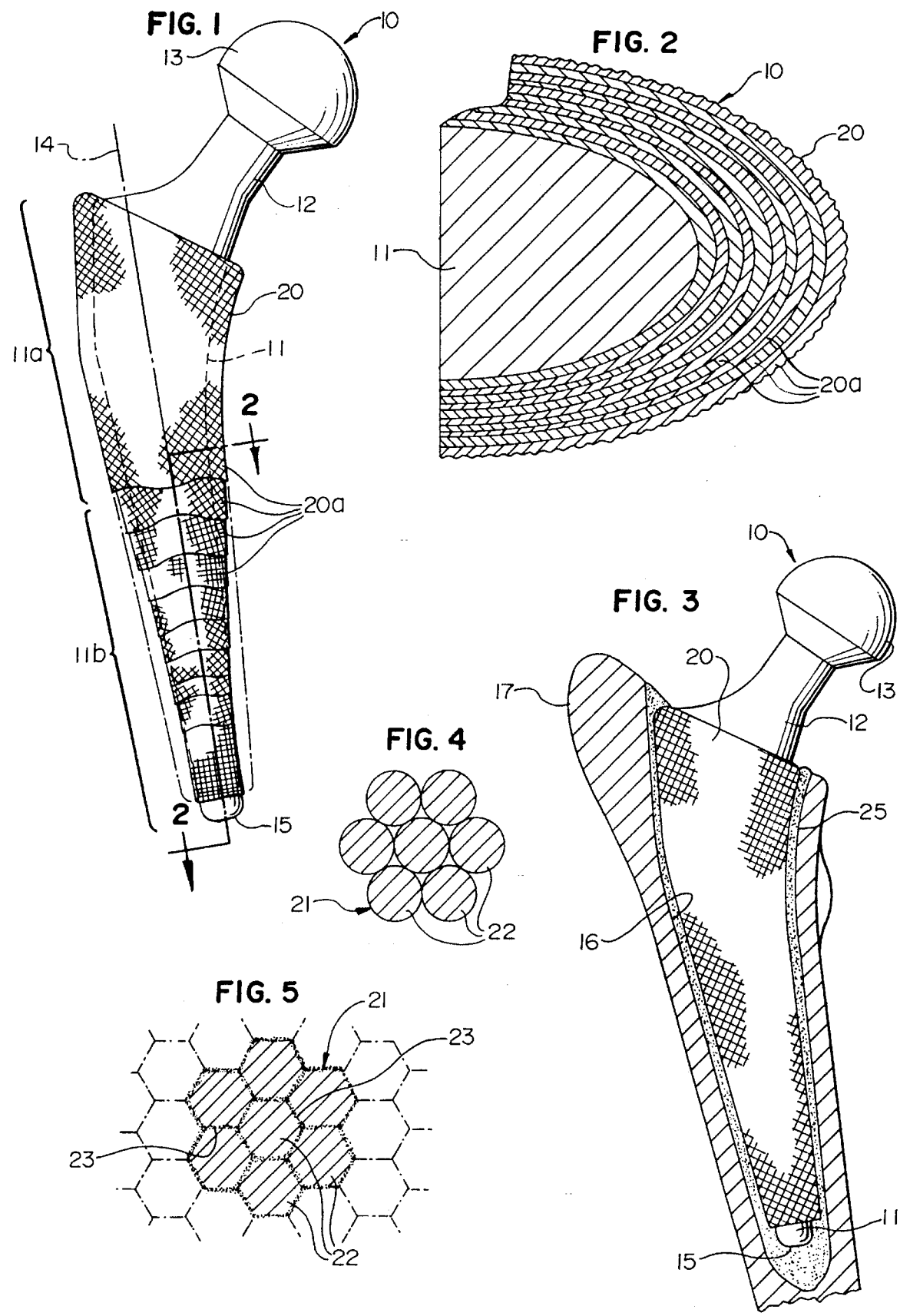

ORTHOPEDIC IMPLANT WITH SELF-REINFORCED MANTLE

BACKGROUND

Poly(methylmethacrylate) (PMMA) has been widely used in orthopedic surgery as a bone cement and has long been known for its superior biocompatability. In a typical orthopedic implant procedure, PMMA cement is used as a grouting agent to fix the rigid stem (usually metal) of a prosthesis in the intramedullary canal of a bone such as, for example, the femur (as in total hip arthroplasty). PMMA bone cement conventionally includes an acrylic polymeric powder which is mixed in the operating room with a liquid acrylic monomer system to provide a dough mass. The doughy mass is inserted into the prepared intramedullary cavity and then, while the cementitious mixture is still in a semi-fluid state, the stem of the prosthesis is fitted into the canal. Within a few minutes, polymerization converts the semi-fluid grout into a hardened mantle.

Despite its advantages in terms of biocompatability, PMMA cement is relatively weak (compared to the bone and the implanted stem) and is frequently found unable to withstand the long-term cyclic loading experienced by a prosthetic joint. Over time, fatigue cracking of the cement mantle may occur along with breakdown of the metal-cement interface. Such fatigue cracking may progress to the point at which there is a loss of support of the metal stem in the canal, resulting in the device becoming loose, unstable and painful. The ultimate result may be a need for replacement of the prosthesis, a difficult and painful procedure.

Another limiting aspect of PMMA as an orthopedic cement material is that there are significant drawbacks to having such cement polymerize in the body cavity. Sufficient heat may evolve during the setting reaction to cause tissue damage and necrosis. Also, the monomer itself has been considered toxic and, if it diffuses from the polymerizing mass, local as well as systemic effects can result (including death). During polymerization, there is an associated shrinkage of the PMMA cement of as much as 10% and such shrinkage may cause residual stresses and premature failure of the mantle. Also, during insertion of the prosthetic stem into an intramedullary canal, it is difficult to assure an optimal mantle thickness of about 2 to 4 mm everywhere about the stem and, if substantial variations occur, the non-uniform thickness may accelerate fracture and fragmentation of the mantle.

Some of these problems are discussed in U.S. Pat. No. 4,491,987. In an effort to improve the interfacial bond between the stem of a prosthesis and the bone cement applied at the time of implantation, the patent teaches that the stem, preferably textured or manufactured with a porous outer surface, should be precoated with a thin layer of PMMA. Because of the precoating, a lesser amount of new bone cement is employed during the subsequent surgical procedure. The exotherm of the reaction is thus limited, decreasing the probability of necrosis and reducing the possibility of systemic interference resulting from toxic monomer.

While such a precoat enhances implant-cement interfacial strength by having the new cement bond to the PMMA precoat (instead of directly to the metal or ceramic stem) during implantation, the mechanical properties of the acrylic precoat in terms of strength, modulus, and fracture toughness are not notably superior to those of bulk acrylic.

Considerable effort has been expended to improve the properties of PMMA so that its fatigue behavior more closely matches that of a prostheses it fixes in place. Some of that effort has involved the reinforcement of PMMA with high strength fibers of stainless steel, carbon, or Kevlar. See B. M. Fishbane and S. R. Pond, *Clin. Orthop. Rel. Res.*, Vol. 128, p. 194 (1977); R. M. Pilliar and R. Blackwell, *J. Biomed. Mater. Res.*, Vol. 10, p. 893; S. Saha and S. Pal, *Trans. 7th Ann. Soc. Biomater.*, Vol. 4, p. 21 (1981). However, the inclusion of such fibers in a composite bone cement tends to increase the viscosity of the semi-fluid mixture, making application more difficult and increasing the possibility that objectionable voids or windows may occur in the cement mantle. Also, the properties of these composites are controlled by the strength of the fiber-matrix bond which, for the fibers mentioned, is fairly low.

Whether such fibers are incorporated in the acrylic cement applied at the time of surgery or in a precoat applied to the stem of a prosthesis, they introduce an additional material that may create or complicate problems of biocompatability. Such concerns would be reduced if the reinforcing fibers in a PMMA cement matrix were of a like material.

A process for producing higher-strength PMMA fibers for possible use in reinforcing a PMMA matrix has been described in an article by C. A. Buckley, E. P. Lautenschlager and J. L. Gilbert in *J. Applied Polymer Science*, Vol. 44, pp. 1321–1330 (1992), the disclosure of which is incorporated by reference herein. In that process, PMMA was drawn into fibers by melt extrusion followed immediately by a transient temperature drawing process. By adjusting processing variables, fibers ranging from 25 µm to 635 µm in diameter were produced. Those fibers produced by a relatively slow extrusion speed and small extrusion hole diameter combined with a relatively fast draw rate were found to have the highest degree of molecular orientation or alignment as reflected by their relatively high heat relaxation ratios. Both tensile strength (Ultimate Tensile Strength) and modulus increased dramatically with greater molecular orientation, as reflected by length relaxation ratios. For example, a maximum UTS of 225 MPa (megapascals) was observed in a fiber of 36 µm diameter having a length relaxation ratio of 18.7 to 1, representing approximately a 600% increase in strength over bulk PMMA material.

Other references indicating the state of the art are U.S. Pat. Nos. 4,963,151, 4,735,625, 5,037,442, 4,895,573, 3,992,725, 4,718,910, 4,851,004, 5,080,680, 5,180,395, 5,197,990, 4,743,257 and 5,171,288.

SUMMARY OF THE INVENTION

One aspect of this invention lies in the recognition that while PMMA fibers of high strength and superior mechanical properties may be produced by melt-extrusion followed by simultaneous drawing and cooling, so that such fibers have longitudinally-oriented molecular chains and a draw ratio, as measured by heat relaxation, of no less than about 6 to 1, the inclusion of such fibers as a reinforcing additive to PMMA cement necessarily fails to utilize, at least to full advantage, the high-strength characteristics of such fibers because, among other things, such fibers are subject to partial or complete dissolution in the monomer used in preparing the PMMA matrix. This invention involves the further recognition that such high-strength PMMA fibers could be far more effectively used in the fabrication of a self-reinforced polymeric mantle encasing the stem of a joint prosthesis, with such fibers retaining their integrity and molecular orientation and with adjacent fibers being interlocked against relative movement.

The fibers of a mantle embodying this invention extend in predetermined directions relative to the stem of an implant to take advantage of substantial increases in strength, fatigue resistance, and fracture toughness resulting from their molecular orientation. Since the advantageous mechanical properties of the fibers results from the manner in which they are produced, with such properties being ultimately controlled by fiber diameter, the mantle should be composed of fibers of relatively small diameter within the general range of about 5 to 500 μm with each fiber having molecular alignment resulting in a heat relaxation ratio (in length) of no less than about 6 to 1.

The mantle may be formed by wrapping the oriented fibers, or strands composed of a multiplicity (5 to 30) of such fibers, in selected directions about the stem of the prosthesis or, alternatively, preforming the fibers or the multi-fiber strands into a mat or sleeve that is wrapped or fitted about the stem at the time of manufacture. In any case, the fibers extend in controlled directions to form a multi-layered pre-mantle. The pre-mantle is then heated with compressive constraint to sinter and interlock the fibers together at their points or lines of contact without substantially reducing or relieving their molecular orientation, thereby producing a textured mantle of connected, contracted, and oriented polymeric fibers about the stem or bone-implantable element of the prosthesis. In that connection, it is to be emphasized that sintering not only locks the fibers together but, because of limited heat relaxation, causes slight contraction of the fibers and such contraction serves to draw the mantle tightly about the stem.

If desired, a PMMA precoat as disclosed in U.S. Pat. No. 4,491,987 may be applied to the stem prior to application of the mantle of self-reinforced molecularly-oriented fibers. In any event, the thickness of the fibrous mantle should be substantial, the average thickness falling within the range of about 1 to 4 mm and preferably 2 to 2.5 mm, so that a lesser amount of PMMA grout is required at the time of implantation (as compared with conventional practice). The reduced amount of cement required at the time of implantation reduces the exotherm and the incidence of toxic substance to which the body is exposed, while the preformed mantle insures that the stem is encased in PMMA and that direct contact between the metallic stem and the intramedullary wall does not occur. Since the cement applied at the time of implantation is compositionally identical, or at least chemically bondable, to the fibrous mantle, the monomer of the polymeric mixture used as the grouting material softens and bonds with the outermost stratum of the mantle, thereby integrating the mantle with the applied cement.

The term "PMMA bone cement" is used here to mean a conventional acrylic cement formed from a two component system with one of such components comprising polymethylmethacrylate or methylmethacrylate-styrene copolymer in powder form. The powder is mixed with a liquid monomer, such as methylmethacrylate, which generally also includes initiators and inhibitors such as N,N-dimethyl-p-toluidine and hydroquinone. Barium sulfate may be incorporated in the powder to render the cement radio-opaque.

DRAWINGS

FIG. 1 is an elevational view of the femoral component of a total hip prosthesis having a preformed self-reinforced fibrous mantle. Certain layers of the mantle are cut away to reveal the multi-layer construction in which fibers, or strands composed of multiple fibers, extend in different selected directions.

FIG. 2 is an enlarged fragmentary cross sectional view taken along line 2—2 of FIG. 1.

FIG. 3 is a partial vertical cross sectional view of the femoral prosthesis in implanted condition.

FIG. 4 is an enlarged fragmentary sectional view of a multiple-fiber strand prior to incorporation in a mantle and constrained sintering thereof.

FIG. 5 is a fragmentary sectional view schematically depicting such strand after mantle incorporation and sintering under pressure.

DETAILED DESCRIPTION OF PREFERRED EMBODIMENTS

Figure 6:
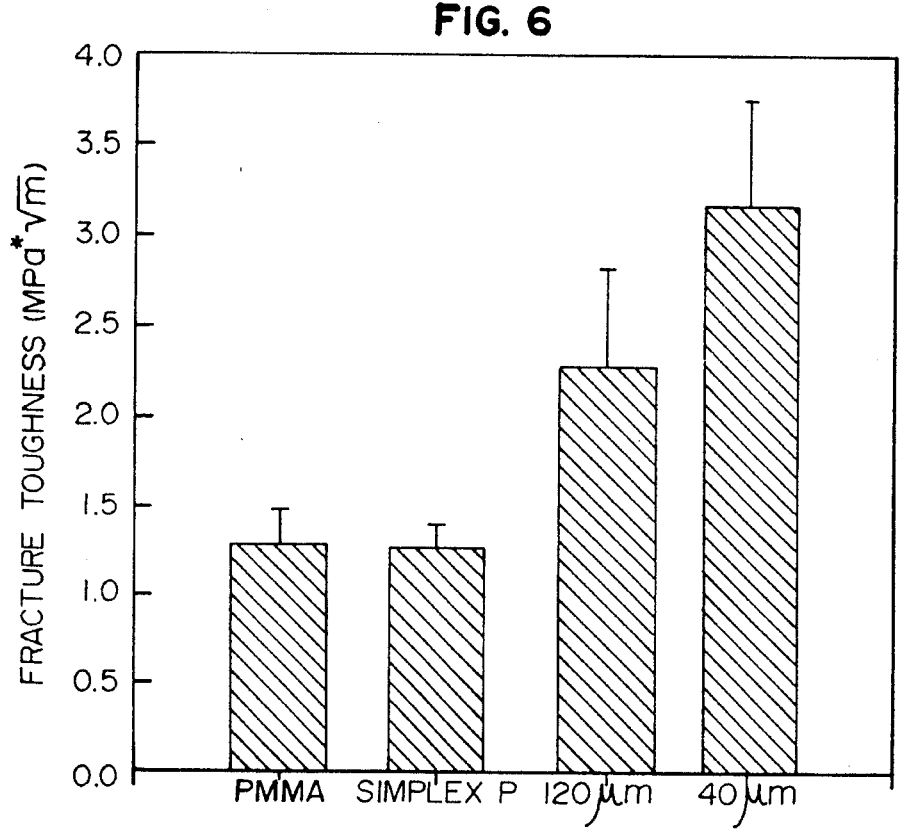
FIG. 6 is a graph depicting the results of fracture toughness tests conducted on samples composed of self-reinforced uni-directional fibers prepared in accordance with this invention and compared with samples of bulk PMMA and conventional bone cement.

Referring to the embodiment in FIGS. 1–5, the numeral 10 generally designates the femoral component of a total hip prosthesis having a stem 11, an angular neck portion 12 integral with the stem, and a proximal ball 13. The stem tapers along a primary axis 14 towards a reduced distal end 15 and may generally be considered to include proximal and distal portions 11a and 11b, respectively. As shown in FIG. 3, the stem is dimensioned to be received in the intramedullary canal or cavity 16 of a femur 17. While a femoral implant is depicted for purposes of illustration, it will be understood that this invention is not limited to a hip prosthesis but is applicable to any orthopedic prosthesis, particularly a joint prosthesis, having a rigid stem dimensioned to be received in the intramedullary cavity of a bone. For example, finger, knee, shoulder and elbow prostheses may benefit from the invention as hereinafter described.

The prosthesis component 11 as so far described is entirely conventional. The particular materials from which the stem, neck, and ball are formed are not critical insofar as the present invention is concerned as long as the prosthesis possesses the requisite strength characteristics. Metal alloys such as stainless steels, titanium and cobalt-chromium alloys are typical and preferred but, if desired, the prosthesis may be fabricated from ceramics or from a combination of metal alloys and polymers such as high-density polyethylene, polytetrofluoroethylene and the like. The stem of the prosthesis may include a thin PMMA precoating (not shown) applied at the time of manufacture as disclosed in U.S. Pat. No. 4,491,987. As described in that patent, such a prosthesis is preferably manufactured from a chromium-cobalt alloy such as Vitallium with the stem portions of the prosthesis that receive the PMMA precoat being pretreated with sulfuric acid, sandblasting, or the like to prepare fresh, rough, metallic surfaces. If such precoating is omitted, then the surfaces of the metallic stem may be either smooth or roughened.

A preformed self-reinforced polymeric mantle 20 encases at least a substantial portion of the length of stem 11. In the illustrated embodiment, the mantle is in the form of a sleeve that extends substantially the full length of the stem; however, other embodiments may include, but are not limited to, only distal coverage, or possibly two spaced locations of coverage—one proximal and the other distal. It is also contemplated that a lesser portion of the stem can be encased by the mantle and, in particular, that only proximal portion 11a of the stem may be so covered while still achieving many if not all of the major advantages described herein.

Mantle 20 is composed of multiple layers of self-reinforced PMMA fibers, such fibers being melt-extruded and simultaneously drawn and cooled to produce longitudinally-oriented molecular chains, all in accordance with the process disclosed in the aforementioned publication by C. A. Buckley, E. P. Lautenschlager, and J. L. Gilbert, *J. Applied Polymer Science*, Vol. 44, pp. 1321–1330 (1992). The fibers should be of a diameter within the range of about 5 to 500 µm and have a drawn ratio, as measured by length heat relaxation, of no less than about 6 to 1. The degree of length heat relaxation is determined by heating a cut section of a fiber above its glass transition temperature (about 110° C.) until the nonequilibrium "frozen in" molecular alignment of the longitudinally-extending polymer chains is released and the chains return to their random coil configuration, resulting in a decrease in fiber length and an increase in fiber diameter. Relaxation may be considered complete when the bending and twisting associated with relaxation ceases and the fiber section lays flat and straight for an extended period of time at a temperature above the glass transition temperature. After cooling of the fiber section, the relaxation ratio may then be calculated by measuring the final length of the fiber section and comparing the same with its initial length. The higher the heat relaxation ratio as so developed, the greater the longitudinal orientation of the molecular chains of the fiber prior to testing. While the ratio for the PMMA fibers used in the mantle of this invention should be no less than about 6 to 1, higher ratios of 18 to 1 or more are preferred.

Acceptable fiber diameters of about 5 to 500 µm define a general range, but a more specific range for achieving the benefits of this invention is 20 to 150 µm, with about 30 to 100 µm being a preferred range. It is believed that the molecular weight of the PMMA may be of an average between 100,000 and 1,000,000, although particularly effective results have been obtained where the average molecular weight is approximately 200,000.

The oriented PMMA fibers used in fabricating the self-reinforced mantle 20 may also be characterized by their relatively high ultimate tensile strength, fracture toughness, and fatigue resistance as compared with unoriented bulk PMMA. In general, such fibers should have ultimate tensile strengths of at least 100 MPa (bulk PMMA of medium molecular weight is of about 25–30 MPa), and preferably at least 200 MPa; fracture toughness ($K_{1c}$) of at least 1.5 (MPa$\sqrt{}$m) and preferably at least 2.5 (MPa$\sqrt{}$m); and fatigue resistance of at least 50 MPa at $10^6$ cycles (bulk PMMA of medium molecular weight is of about 20 MPa at $10^6$ cycles), and preferably at least 70 MPa at $10^6$ cycles.

The orientation of the fibers in relation to the stem of the prosthesis is important for effectively resisting the stresses of in-vivo loading. Since the molecular alignment strengthens or self-reinforces the fibers in longitudinal directions, a primary objective is that there be an abundance of fibers oriented parallel to the principal stress directions. It has been indicated that with a conventional femoral implant, the stress directions in at least the upper (proximal) portion of the stem are generally in planes normal to the longitudinal axis of that stem. Therefore, while it is believed important to have the fibers of the mantle extend in a plurality of predetermined directions, there should be an abundance of fibers in that portion of the mantle surrounding the proximal portion 11a of the stem that extend in planes that are approximately normal or perpendicular to axis 14. There should also be other fibers extending longitudinally and in other directions in relation to the stem so that when taken as a whole the mantle has fibers extending in a multiplicity of different directions in what might be regarded as "quasi-isotropic" orientation, in contrast to uni-directional orientation.

It is believed that these objectives are most effectively achieved by arranging the fibers into a multi-layered woven mat or fabric extending about the stem of the prosthesis. Because of the small diameter of the fibers, and for other reasons such as ease of application to the stem, it is considered beneficial to weave the layers of the mantle from strands of fibers, each strand containing a multiplicity (5 to 30) of such fibers. To illustrate, FIG. 4 shows such a strand 21 composed of seven PMMA fibers having the self-reinforcing characteristics described. The fibers are shown as being generally uni-directional in each strand but it should be understood that some variations are permissible; for example, the fibers of the strand may be twisted together or one strand may be wrapped about the rest of the strands which remain generally parallel to each other. The strands so formed are then woven, preferably in a conventional over-under pattern, to produce a fabric which becomes one layer of the multi-layered mantle. Each layer is arranged so that its fibrous strands extend in predetermined directions with respect to the axis of the mantle to provide the quasi-isotropic orientation mentioned above. If desired, the mantle may be woven into a sleeve upon a mandrel dimensioned to correspond with the size and shape of a prosthetic stem and, when completed, the preformed multi-layered sleeve may be removed from the mandrel and fitted onto the stem into the position shown.

The number of layers should be sufficient to insure quasi-isotropic fiber orientation with particular emphasis on providing an abundance of fibers extending in planes generally parallel with the stress trajectories of in-vivo loading. It is believed that most effective results are obtained if the number of such layers is in the range of 5 to 15. In the embodiment illustrated, mantle 20 is shown to be composed of 10 such layers or strata 20a, but a greater or smaller number may be provided as long as the reinforcing effect of the preformed mantle is not compromised and the average thickness of the resulting multi-layered mantle is 1 to 4 mm, and preferably about 2 to 2.5 mm.

Completion of the mantle is not achieved until the fibers are locked together in partially contracted condition by a sintering operation. The term "sintering" is used here to include diffusion bonding; that is, adjacent fibers may become fused together along their length or at points of intersection either as a result of the incipient melting of their outer surfaces or by reason by intermolecular diffusion resulting from such heat treatment. The sintering results only in a molecular relaxation of the outer surface of each fiber without substantially reducing the molecular orientation or alignment throughout the body or core of each fiber. Some limited longitudinal contractions of each fiber necessarily occurs but the effect is advantageous because it draws the fibers, strands and successive layers of the mantle into tight interlocking engagement with each other and into firm contractive engagment with the stem about which the mantle extends.

FIG. 5 schematically illustrates the effect of sintering upon a strand 21 of seven fibers 22, the arrangement of fibers being the same as previously described in connection with FIG. 4. Because of peripheral heat relaxation and pressure, each fiber, originally of circular cross section, assumes a hexagonal configuration with the surfaces of adjacent fibers being fused together as indicated at 23.

The sintering conditions may be varied to achieve maximum fiber-to-fiber bonding with maximum retained molecular orientation, but it has been found that such sintering should include the application of pressure to what may be referred to as an unsintered pre-mantle. Such pressurization may be achieved by compressing the unsintered pre-mantle encasing stem 11 by two (or more) heated mold sections or by vacuum bagging and heating the stem and pre-mantle in an autoclave. In either case, the sintering should occur at temperatures within the range of about 110° to 140° C. (preferably 120° to 125° C.) for periods of 10 to 30 minutes (preferably 15 to 25 minutes) and at gauge pressures of about 1 to 5 atmospheres (preferably about 2 atmospheres). The final result, following the sintering procedure, is an integrated self-reinforced mantle of high-strength oriented PMMA fibers that are contracted, interconnected, and tightly encasing the stem 11 of the prosthesis. Because the strands of fibers are interwoven, the outer surface of the mantle 20 is textured as indicated in FIG. 2. It may also be slightly porous, depending on the sizes of the strands, the closeness of the weave, and the conditions of sintering.

Mantle 20 is a true mantle because of its substantial thickness (in contrast to a precoat) and because it may interface directly with the intramedullary surface of the bone into which it is received. If the prosthesis is to be implanted without bone cement, it is desirable that the mantle's outer surface not only be textured but also porous, thereby promoting bone ingrowth. Preferably, however, the intramedullary canal is reamed and prepared to be slightly larger than the mantle-equipped prosthesis to accommodate a layer of bone cement applied at the time of implantation. Such a layer is designated by numeral 25 in FIG. 3. Because the mantle is compositionally the same as, or is at least chemically bondable to, the applied PMMA cement, a secure bond occurs between the thin layer of grouting cement and the preformed mantle. Since a relatively small amount of cement 25 is required, the exotherm of the reaction is lessened, decreasing the possibility of tissue necrosis, and a minimal amount of toxic monomer is involved. Such monomer nevertheless constitutes a solvent for the fibrous mantle and, consequently, an outer layer or strata of the mantle becomes chemically bonded to the PMMA cement grouting as that grouting polymerizes.

The PMMA cement applied at the time of implantation may be any approved, self-curing, PMMA bone cement composition. One such composition is marketed by Howmedica, Inc., Rutherford, N.J., under the designation "Simplex-P" and is a two-component system which includes a powder (16.7% PMMA and 83.3% methylmethacrylate-styrene copolymer) and a liquid consisting primarily of methylmethacrylate monomer. Another approved self-curing bone cement is marketed by Zimmer U.P.S.A., Warsaw, Ind. and is also a two-component system in which the powder component is over 99% PMMA and the liquid component is primarily methylmethacrylate monomer.

The following examples further illustrate various aspects of this invention.

EXAMPLE 1

Two groups of test samples were prepared from unidirectional molecularly-oriented PMMA fibers sintered together, the samples of one group being formed from fibers of 40 μm diameter and those of the other from fibers of 120 μm diameter. The fibers were formed by melt extrusion accompanied by simultaneous drawing and cooling of the PMMA to produce fibers with longitudinally-oriented molecular chains, the drawn length relaxation ratios of such fibers being approximately 15 to 18 for the 40 μm fibers and 11 to 15 for the 120 μm fibers. The fibers were then arranged in parallel and sintered at a temperature of about 125° C. for 25 minutes at a pressure of about 3 atmospheres. After cooling, test samples measuring 20 mm by 10.5 mm by 2.5 mm were cut for evaluation of flexural strength and fracture toughness. Samples of similar size of Simplex-P bone cement (Howmedica, Inc., Rutherford, New Jersey) and commercially-available PMMA sheet materials were also fabricated for comparison. A minimum of 5 samples of each material were prepared for three-point flexure tests and fracture toughness tests.

The three-point flexure tests and the fracture toughness tests were performed at a crosshead speed of 7.6 mm/sec and 2.54 mm/sec, respectively. In the fracture toughness tests, a single edge notched geometry was used and a pre-crack was imparted to the samples by way of a slow speed diamond saw, followed by cutting with a razor blade.

The results of the three-point flexure tests are presented in the following table:

| | Three-Point Flexure Results (mean ± SD) | | |
|---|---|---|---|
| Type of Material | Maximum Stress (MPa) | Modulus (GPa) | Elongation (%) |
| PMMA | 128.5 ± 11.4 | 2.67 ± 0.25 | 9.0 ± 1.3 |
| Simplex | 84.5 ± 5.2 | 2.63 ± 0.18 | 5.6 ± 0.8 |
| 120 μm | 118.4 ± 12.7 | 2.8 ± 0.12 | 35.3 ± 2.9 |
| 40 μm | 129 ± 14.0 | 2.75 ± 0.11 | 30.3 ± 4.9 |

In terms of bend strength, only the Simplex-P was statistically different from the other groups and there were no significant differences in modulus between groups. It will be noted, however, that the percent elongation was significantly greater for the samples composed of self-reinforced fibers than for the samples of PMMA and Simplex-P.

The fracture toughness test results are as follows:

| Fracture Toughness Results (mean ± SD) | |
|---|---|
| Type of Material | $K_{1c}$ (MPa$\sqrt{m}$) |
| PMMA | 1.28 ± 0.2 |
| Simplex-P | 1.27 ± 0.12 |
| 120 μm | 2.27 ± 0.54 |
| 40 μm | 3.17 ± 0.57 |

The comparative results also appear in bar graph form in FIG. 6. It can be seen that the fracture toughness values are significantly larger for the samples of self-reinforced PMMA fibers than for the Simplex-P and PMMA samples. Those samples composed of fibers of 40 μm had the highest fracture toughness values, nearly three times the fracture toughness for Simplex-P.

The differences in the data developed from these tests as revealed by the two tables and graph indicate that while the fibrous samples did not appear superior with regard to crack initiation, they were notably superior in resisting crack propagation. Optical and SEM evaluation of the fracture surfaces reveal that while the PMMA and Simplex-P samples had relatively smooth fracture surfaces perpendicular to the tensile stress axis, the self-reinforced fibrous samples showed significant crack splitting and branching in both tests. The fracture toughness results can therefore be explained by the crack branching and fiber splitting processes which divert the crack front and significantly increase the damage energy dissipated prior to failure.

EXAMPLE 2

Fourteen samples of each of four materials were prepared as described for the three point flexure test in Example 1. Each sample was thereafter subjected to three-point flexure as previously described except that an oscillatory loading at 5 Hz at an R ratio (minimum load over maximum load) of 0.1 was used to test each sample for flexural fatigue. Such flexural fatigue tests were performed in air and the data were used to generate S-N curves using the staircase method.

During the flexural fatigue tests, several parameters were tracked over each test using computer data acquisition techniques. These included maximum deflection, modulus, and hysteretic energy loss per cycle. Such data were then used to assess the damage processes present.

Figure 7:
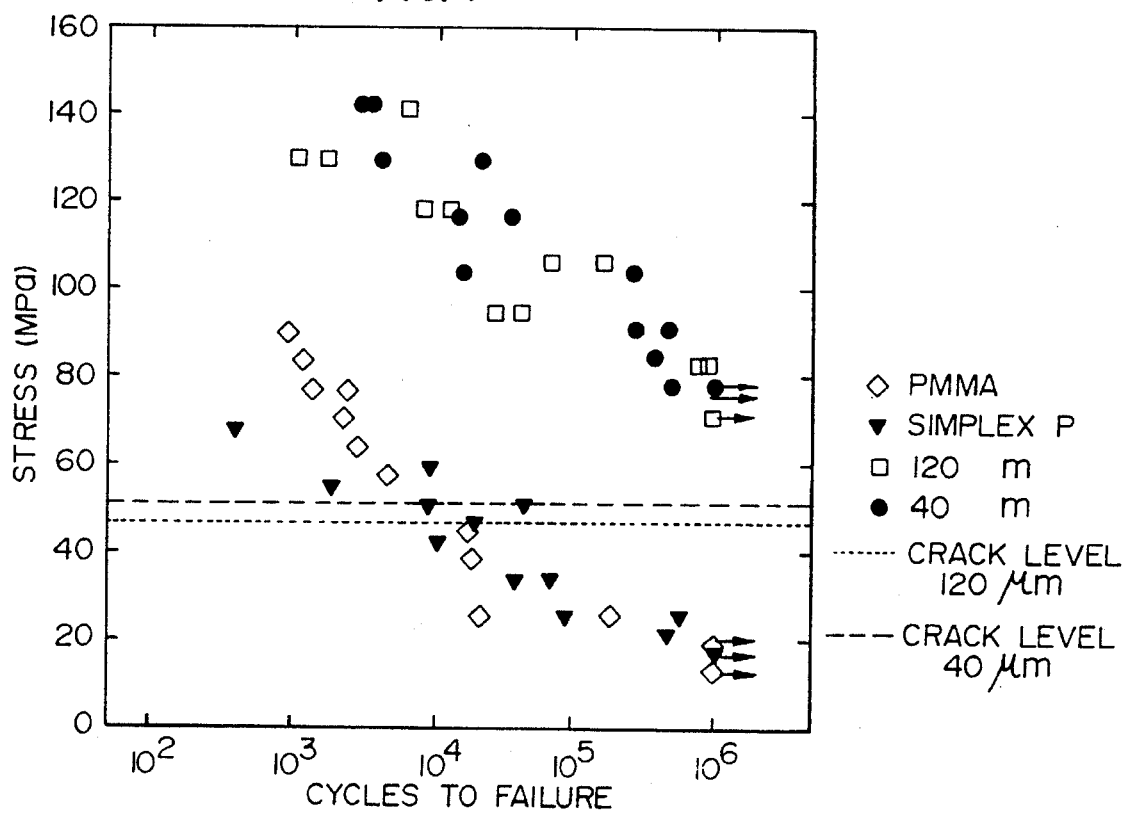
FIG. 7 is a plot depicting the results of flexural fatigue tests conducted on samples of the type described above.

The fatigue test results are shown in FIG. 7. This S-N curve shows that the fatigue strength for the self-reinforced fibrous samples of both sizes (fibers of 40 μm and 120 μm) was about 80 MPa at $10^6$ cycles, whereas the PMMA and Simplex-P samples had fatigue strengths of about 20 MPa. The self-reinforced fibrous samples therefore revealed about a four-fold improvement in fatigue resistance over the non-fibrous samples. Plots of the total hysteretic energy loss for each test showed that the total damage energy dissipated at 1,000,000 cycles was on the order of $10^3$J (Joules) for the fibrous samples while PMMA and Simplex-P only dissipated about 80J before failure.

For the reasons given in Example 1, the flexural fatigue results can be explained by crack branching and fibrous splitting processes for the fibrous samples, diverting the crack fronts and significantly increasing the damage energy dissipated prior to failure. That is further supported by the hysteretic energy loss versus cycles to failure for the fatigue tests which showed a much higher ability of the fibrous samples to absorb energy prior to failure.

EXAMPLE 3

Two woven fabrics composed of high strength PMMA fibers of 40 μm diameter and 120 μm diameter, respectively, for use in making self-reinforced preformed mantles for femoral prostheses in accordance with this invention, may be prepared as follows:

Pieces of commercially available PMMA (Cadillac Plastics, Inc.) of approximately $2 \times 10^5$ molecular weight are heated in an extruder to 169° C. by means of an electric heater and are extruded through a die at a constant rate with the extruded fiber being cooled in air (about 25° C.) and taken up on a drum located immediately adjacent the die's extrusion hole of selected diameter ($d_e$) at a draw velocity ($V_d$) substantially greater than the extrusion velocity ($V_e$). The fiber of 40 μm can be formed by drawing through a die having a die diameter $d_e$ of 0.1 cm at an extrusion velocity $V_e$ of 0.0254 cm/min and a drawn velocity $V_d$ of 12 m/min to produce an oriented high-strength PMMA fiber having a length relaxation ratio of about 15 to 18. The 120 μm fiber can be formed by drawing through a die having a $d_e$ of 0.1 cm at a $V_e$ of 0.0254 cm/min and a $V_d$ of 5 m/min to produce an oriented high-strength PMMA fiber having a length relaxation ratio of about 11 to 15. The ultimate tensile strengths of such fibers are about MPa for the 40 μm fiber and 120 MPa for the 120 μm fiber. Such procedures are essentially the same as used for preparing test samples composed of uni-directional 40 μm and 120 μm fibers as tested in Examples 1 and 2.

To facilitate further processing, the 40 μm fibers may then be formed into strands of 5 to 15 fibers each with one of the fibers wrapped about the remaining parallel fibers to maintain the integrity of the strand. Strands composed of 120 μm fibers are similarly formed with 5 to 10 fibers in each strand. The strands are then woven at right angles in an over-under pattern (or in any other suitable pattern) to produce two rolls or sheets of fabric, one being formed of woven strands composed of oriented high-strength 40 μm PMMA fibers and the other being formed of woven strands composed of oriented high-strength 120 μm PMMA fibers.

EXAMPLE 4

Femoral prostheses provided with self-reinforced mantles of oriented high-strength PMMA fibers woven into fabrics in accordance with Example 3 may be prepared as follows:

A woven fabric composed of 40 μm fibers prepared as in Example 3 is wrapped tightly about the stem of a metal (Vitallium) femoral prosthesis with the fibers at the commencement of the wrapping extending longitudinally and transversely to the main (longitudinal) axis of the stem. As wrapping is continued to produce multiple layers, the taper of the stem results in angular displacement of the fibers of successive layers with respect to the stem's axis, resulting in a quasi-isotropic orientation of the fibers when the wrapping is completed, at which time the thickness of the pre-mantle is approximately 2.5 mm and the number of layers in the wrapping is approximately 8 to 12. The layers are temporarily held in place by further processing, and the femoral prosthesis with the pre-mantle wrapped about its stem is sealed in a vacuum bag which is then placed in a heating chamber (autoclave). A vacuum of 2 to 3 atmospheres is drawn in the bag and the chamber and its contents are heated at a temperature of 125° C. for 20 to 25 minutes. The completed femoral prosthesis with its sintered fibrous mantle contracted tightly about the stem and with the fibers retaining most of their original molecular orientation but now interlocked together, is then removed from the chamber and vacuum bag.

The same procedure is followed in making a femoral prosthesis with a PMMA mantle composed of a fabric wrapping of 120 μm fibers except that a lesser number of layers (approximately 6 to 8) is required to provide the same total thickness of 2.5 mm.

While in the foregoing we have disclosed embodiments of this invention in considerable detail for purposes of illustration, it will be understood by those skilled in the art that many of these details may be varied without departing from the spirit and scope of the invention.

We claim:

1. An orthopedic implant having a rigid stem dimensioned to be received in the intramedullary cavity of a bone; and a self-reinforced polymeric mantle tightly encasing at least a portion of the length of said stem; said mantle being composed of fibers of PMMA that are longitudinally oriented in predetermined directions relative to said stem with each fiber being of a diameter within the range of about 5 to 500 μm and having longitudinally-oriented molecular chains that provide said fiber with a heat relaxation ratio for length of no less than about 6 to 1; adjacent fibers of said mantle having contacting surfaces fused together and which interlocks said fibers against relative movement.

2. The implant of claim 1 in which each of said fibers is formed by melt extrusion followed by simulaneous drawing and cooling for longitudinally orienting the molecules thereof.

3. The implant of claim 1 in which said mantle has a textured outer surface bondable with acrylic bone cement.

4. The implant of claim 1 in which a layer of PMMA bone cement is interposed between said mantle and the surface of said stem.

5. The implant of claim 1 in which said mantle extends about substantially the entire length of said stem.

6. The implant of claim 1 in which said stem has proximal and distal portions; said mantle extending about only said proximal portion.

7. The implant of claim 1 in which a plurality of said fibers are arranged into strands in which the fibers of each strand are generally uni-directional; said strands extending in selected directions along and about said stem and being arranged to provide multiple layers with the strands of different layers extending in different directions.

8. An orthopedic implant having a rigid stem dimensioned to be received in the intramedullary cavity of a bone; and a self-reinforced polymeric mantle tightly encasing at least a portion of the length of said stem; said mantle being composed of fibers of PMMA that are longitudinally oriented in predetermined directions relative to said stem with each fiber being of a diameter within the range of about 5 to 500 µm and having longitudinally-oriented molecular chains that provide said fiber with a heat relaxation ratio for length of no less than about 6 to 1; adjacent fibers of Said mantle having contacting surfaces fused together and which interlocks said fibers against relative movement; a plurality of said fibers being arranged into strands in which the fibers of each strand are generally uni-directional; said strands extending in selected directions along and about said stem and being arranged to provide multiple layers with the strands of different layers extending in different directions; said strands of each layer being interwoven and arranged so that the fibers of each such layer extend in predetermined directions relative to said stem; said fibers of different layers of said mantle extending in different directions than those of adjacent layers.

9. The implant of claims 1 or 7 in which said mantle has an average thickness of about 1 to 4 mm.

10. The implant of claim 9 in which said average thickness is about 2 to 2.5 mm.

11. The implant of claims 1 or 6 in which said fibers are of a diameter within the range of about 20 to 150 µm.

12. The implant of claim 11 in which said fibers are of a diameter within the range of about 30 to 100 µm.

13. The implant of claim 1 in which said PMMA of said mantle has an average molecular weight within the range of about 100,000 to 1,000,000.

14. The implant of claim 13 in which said average molecular weight is about 200,000.

15. The implant of claim 1 in which said fibers have an ultimate longitudinal tensile strength of at least 100 MPa.

16. The implant of claim 7 in which each of said strands contains 5 to 30 of said fibers.

\* \* \* \* \*